(12) United States Patent
Lemmens et al.

(10) Patent No.: US 7,335,380 B2
(45) Date of Patent: Feb. 26, 2008

(54) AMLODIPINE FREE BASE

(75) Inventors: Jacobus M. Lemmens, Mook (NL); Theodorus H. A. Peters, Arnhem (NL); Franciscus B. G. Benneker, Rheden (NL); Rolf Keltjens, Nijmegen (NL)

(73) Assignee: Synthon IP Inc., Gainesville, VA (US)

( * ) Notice: Subject to any disclaimer, the term of this patent is extended or adjusted under 35 U.S.C. 154(b) by 0 days.

(21) Appl. No.: 10/024,520

(22) Filed: Dec. 21, 2001

(65) Prior Publication Data

US 2003/0022922 A1 Jan. 30, 2003

Related U.S. Application Data

(60) Provisional application No. 60/258,613, filed on Dec. 29, 2000.

(51) Int. Cl.
- A61K 9/20 (2006.01)
- A61K 9/22 (2006.01)
- A61K 9/26 (2006.01)
- A61K 31/44 (2006.01)

(52) U.S. Cl. .................. 424/464; 424/465; 424/468; 424/469; 424/470; 514/355; 514/356

(58) Field of Classification Search ................ 424/489, 424/490, 464, 465, 468–470; 514/355–356
See application file for complete search history.

(56) References Cited

U.S. PATENT DOCUMENTS

| 4,572,909 A | 2/1986 | Campbell et al. |
| 4,879,303 A * | 11/1989 | DAvison et al. ............ 514/356 |
| 4,983,740 A | 1/1991 | Peglion et al. |
| 5,155,120 A * | 10/1992 | Lazar et al. ................ 514/356 |
| 5,389,654 A | 2/1995 | Furlan et al. |
| 5,438,145 A | 8/1995 | Furlan et al. |
| 6,046,337 A | 4/2000 | Bozsing et al. |
| 6,057,344 A * | 5/2000 | Young ........................ 514/356 |
| 6,680,334 B2 * | 1/2004 | Bentham et al. ............ 514/355 |

FOREIGN PATENT DOCUMENTS

| EP | 0 089 167 B1 | 10/1986 |
| EP | 0 244 944 | 1/1990 |
| EP | 0 290 211 B1 | 9/1991 |
| EP | 0 534 520 B1 | 3/1997 |
| EP | 0 902 016 A1 | 3/1999 |
| EP | 0 963 980 A2 | 12/1999 |

(Continued)

OTHER PUBLICATIONS

Alker et al., "Long-acting dihydropyridine calcium antagonists. 9. Structure activity relationships around amlodipine", Eur J Med Chem (1991) 26, 907-913.

(Continued)

*Primary Examiner*—Carlos A. Azpuru
(74) *Attorney, Agent, or Firm*—Mark R. Buscher

(57) ABSTRACT

Amlodipine free base can be formulated into a convenient oral dosage form, especially a tablet, without excessive stickiness or tablet punch residue. The amlodipine free base can be crystalline Form I or a novel Form II. Methods of making and using the amlodipine free base are set forth.

18 Claims, 8 Drawing Sheets

FOREIGN PATENT DOCUMENTS

| | | |
|---|---|---|
| EP | 1 181 932 | 2/2002 |
| WO | WO 95/05822 | 3/1995 |
| WO | 99/25688 | 5/1999 |
| WO | 99/52873 | 10/1999 |
| WO | 00/24714 | 5/2000 |
| WO | 00/35873 | 6/2000 |
| WO | 00/35910 | 6/2000 |
| WO | WO 01/74390 | 10/2001 |

OTHER PUBLICATIONS

Amlodipine Besylate Monograph, PHARMEUROPA vol. 10, No. 2, 197-198, Jun. 1998.

Faulkner et al, "Absorption of Amlodipine Unaffected by Food", Arzneim Forsch/Drug Res. 39 (11), No. 7, (1989).

McDaid and Deasy, "Formulation development of a transdermal drug delivery system for amlodipine base", International Journal of Pharmaceutics 133 (1996) 71-83.

Arrowsmith et al., "Long-Acting Dihydropyridine Calcium Antagonists. 1. 2-Alkoxymethyl Derivatives Incorporating Basic Substituents", J. Med. Chem. American Chemical Society, 1986, 29, 1696-1702.

FDA FOIA Material on Amlodipine Besylate, NDA No. 19-787, "Review of an Original NDA", Oct. 10, 1990.

* cited by examiner

AMLODIPINE FREE BASE

This application claims the benefit of priority under 35 U.S.C. §119(e) from provisional patent application Ser. No. 60/258,613, filed Dec. 29, 2000.

BACKGROUND OF THE INVENTION

1. Field of the Invention

The present invention relates to amlodipine free base, compositions comprising amlodipine free base and to use of amlodipine free base in therapy.

2. Description of the Related Arts

EP 089 167 and corresponding U.S. Pat. No. 4,572,909 disclose a class of substituted dihydropyridine derivatives as being useful calcium channel blockers. These patents identify that one of the most preferred compounds is 2-[(2-aminoethoxy)methyl]-4-(2-chlorophenyl)-3-ethoxycarbonyl-5-methoxycarbonyl-6-methyl-1,4-dihydropyridine. This compound, which is now commonly known as amlodipine, has the following formula:

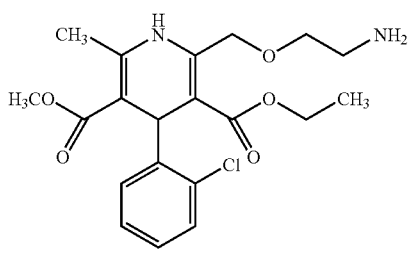

(1)

While amlodipine as a free base and as a pharmaceutically acceptable acid addition salt are generally taught, the amlodipine examples all make amlodipine maleate; e.g. examples 9, 11, 12, and 22 of EP 089 167. The maleate salt is identified as the most preferred acid addition salt. Surprisingly, amlodipine free base is not characterized. The examples appear to describe the formation of the free base but only as a solution/slurry (example 11) or as a residue remaining after evaporation of the solvent (examples 12 and 22). Only the amlodipine maleate salt is described as precipitating from a solution (examples 12 and 22).

Subsequently, EP 244 944 and corresponding U.S. Pat. No. 4,879,303 were issued directed to the besylate (or benzene sulfonate) salt of amlodipine. The besylate salt is stated to provide certain advantages over the known salts including amlodipine maleate. Various amlodipine salts were compared for water solubility, stability, non-hygroscopicity, and processability for tablet formation. Amlodipine free base was included in the processability testing which involved measuring the amount of amlodipine remaining on the tablet punch after making tablets. The amlodipine free base tablets are reported as leaving on the punch an average of 2.02 µg amlodipine/cm² per tablet. The amlodipine besylate tablets are reported as leaving on average 1.17 µg amlodipine/cm² per tablet. Thus, the free base composition suffered from excessive stickiness to the tablet punch and was not as suitable in making solid dosage forms for peroral administration. The amlodipine besylate salt is described in examples 1 and 5 thereof as being made from slurried amlodipine free base although no method is described for how the free base was prepared.

D. M. McDaid and P. B. Deasy in Int. J. of Pharmaceutics 133, 71-83 (1996) suggest the use of amlodipine free base in a transdermal pharmaceutical such as a patch. Amlodipine free base in solid state was prepared in the above article, its structure confirmed by NMR, and it was characterised by a melting point of 144° C. and aqueous solubility of 77.4 mg/l. The solid amlodipine base was prepared by a neutralization of a solution of amlodipine besylate with sodium hydroxide. In a first process, the besylate was dissolved in methanol at 20° C., aqueous sodium hydroxide was added and the base was extracted from the mixture by diethyl ether, which was then evaporated. It should be noted that this process, as described, is irreproducible as diethylether is miscible with the reaction mixture. In a second process, an aqueous solution of the besylate was treated at 50° C. with a sodium hydroxide solution and the base crystallized after cooling to 4° C.

It would be desirable to have an amlodipine oral dosage form based on amlodipine free base. Such a dosage form should preferably be equivalent to amlodipine acid addition salt forms, especially the commercial amlodipine besylate salt, and should not suffer from significant manufacturing or stability problems. Further, it would be desirable to provide a direct method for forming amlodipine free base that can allow for isolation by, inter alia, filtration.

SUMMARY OF THE INVENTION

The present invention is based on the study of amlodipine free base and the discovery of various physical properties thereof. From a realization of these properties, the present invention provides for a useful amlodipine free base pharmaceutical dosage form especially a tablet, a novel crystalline form of amlodipine free base, a population of amlodipine free base particulates that are useful in making a tablet, and a process for more economically forming amlodipine free base. Accordingly, a first aspect of the present invention relates to a pharmaceutical tablet composition comprising an effective amount of amlodipine free base and at least one pharmaceutically acceptable excipient; wherein the tablet exhibits low punch residue, as is defined hereinafter. Preferably the tablet leaves an average residue on the tablet punch of 0.7 µg·cm$^{-2}$ per tablet or less.

Another aspect of the present invention relates to crystalline amlodipine free base form II. This new crystalline form of amlodipine is also suitable for use as the pharmaceutical active agent.

Another aspect of the present invention relates to a population of particulate amlodipine free base having an average particle size of at least 100 microns. Preferably the particulates are crystals and the average particle size is 150 to 350 microns. Such a population of particulates is useful in the formation of a tablet composition.

A further aspect of the invention relates to a method of treating or preventing hypertension, angina, or congestive heart failure, which comprises administering an effective amount of amlodipine free base to a patient in need thereof. Preferably the amlodipine free base is administered in the above-mentioned tablet form.

A still further aspect of the present invention relates to a process which comprises deprotecting an N-protected amlodipine with a deprotecting agent to form amlodipine free base; precipitating said amlodipine free base from a solution; and isolating said precipitated amlodipine free base in solid state form. The solution from which amlodipine free base precipitates can be the solution resulting from the deprotecting step or a different solution; i.e. in an extraction solvent.

Another aspect of the present invention relates to a process for purifying amlodipine free base, which comprises: crystallizing amlodipine free base from a non-aqueous solvent. Advantageously the crystallization produces amlodipine free base crystals having an average particle size of 150 to 350 microns.

BRIEF DESCRIPTION OF THE DRAWINGS

FIG. 4 shows an IR spectrum of crystalline amlodipine free base (Form I) of example 4a.

FIG. 5 shows a DSC curve of crystalline amlodipine free base (Form I) of example 4a.

FIG. 6 shows an IR spectrum of crystalline amlodipine free base (Form II) of example 5a.

FIG. 7 shows a DSC curve of crystalline amlodipine free base (Form II) of example 5a.

DETAILED DESCRIPTION OF THE INVENTION

An amlodpine free base tablet according to the present invention is preferably a low punch residue tablet. A "low punch residue" as used herein means that the average amount of amlodipine left on a tablet punch is not more than 1 µg/cm² per tablet based on a 20 mm round flat punch with a compression force of 15 kilo-newtons. Preferably, the tablet has an average punch residue of 0.7 µg/cm² per tablet, more preferably 0.6 µg/cm² per tablet. The amount of amlodipine residue can be measured by the process described in EP 244 944. In general the method involves washing the punch after runs of 50, 100, 150, 200, 250 and 300 tablets, using methanol and an ultrasonic bath. The amount of amlodipine in the samples is measured by uv and the total amount of amlodipine extracted from both the upper and lower punch is plotted against the amount of tablets made. An average value for amlodipine residue (stickiness) is calculated from the slope of the regression line by forcing the y-intercept of the line through zero.

The tablet comprises an effective amount of amlodpine free base and at least one pharmaceutically acceptable excipient. An "excipient" as used herein means any pharmaceutically acceptable inactive component of the composition. As is well known in the art, excipients include diluents, binders, lubricants, disintegrants, colorants, antioxidants/preservatives, pH-adjusters etc. The excipients are selected based on the desired physical aspects of the final form: e.g., obtaining a tablet with desired hardness and friability, being rapidly dispersible and easily swallowed, etc. The desired release rate of the active substance from the composition after its ingestion also plays a role in the choice of excipients. For example, preparations may, if desired, be designed to give slow release of the amlodipine free base.

Suitable excipients for use in this invention include:
a diluent such as calcium hydrogen phosphate, lactose, mannitol etc.
a binder such as microcrystalline cellulose or a modified cellulose, povidone etc.
a disintegrant such as sodium starch glycollate, crosspovidone
a lubricant such as magnesium stearate, sodium stearyl fumarate, talc
a colorant, taste masking agent, etc.

The tablets of the invention preferably do not require any anti-sticking agent such as talc. The composition of the tablet preferably comprises a calcium phosphate excipient and/or microcrystalline cellulose and more preferably both a calcium phosphate and microcrystalline cellulose. An example of a calcium phosphate excipient is anhydrous calcium hydrogen phosphate. In addition, the tablet may contain other conventional excipients such as binders, lubricants, disintegrants, colourants, preservatives etc.

Figure 1:
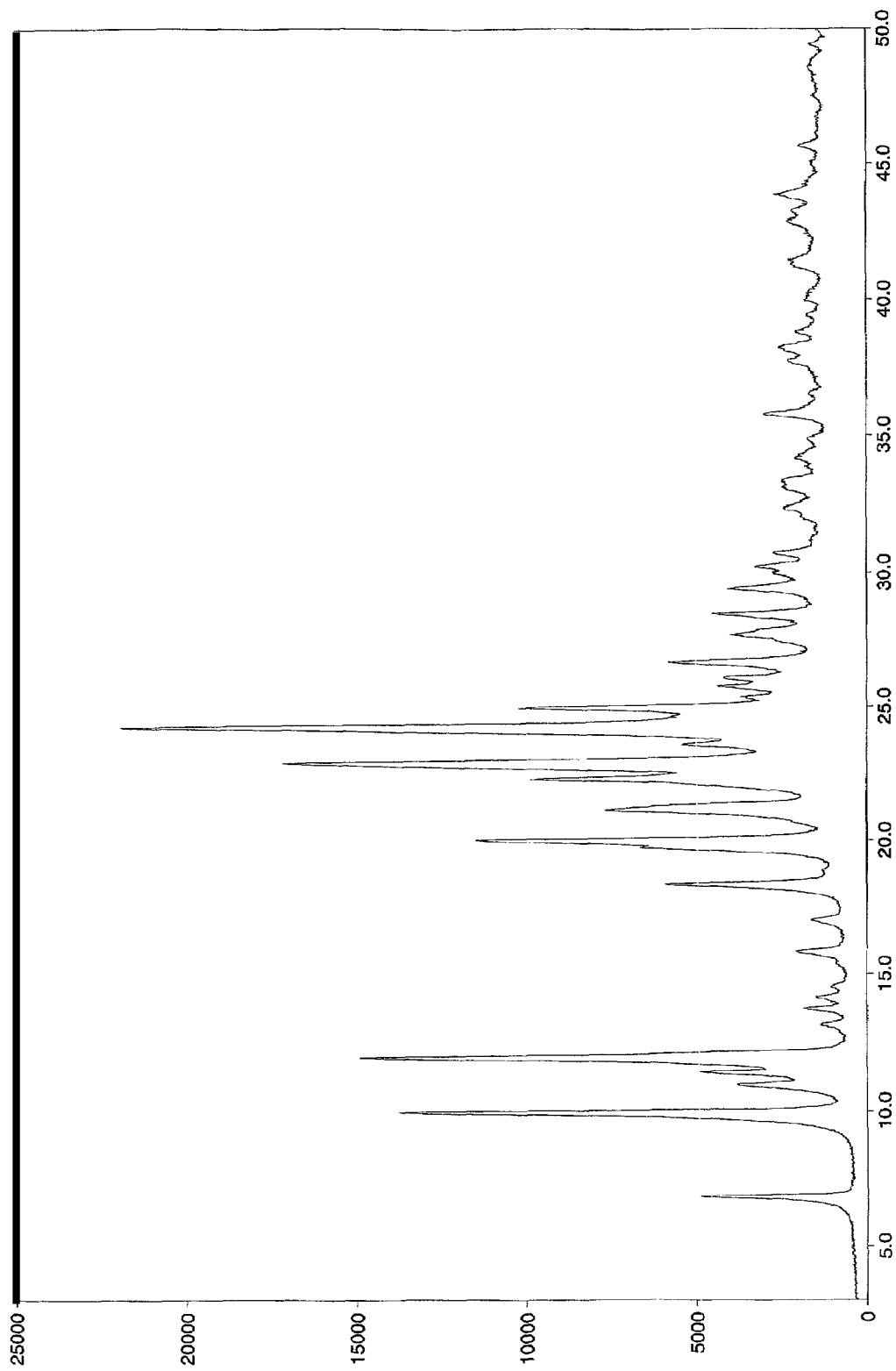
FIG. 1 shows a powder x-ray diffractogram for the amlodipine free base (Form I) of reference example 3.
Figure 2:
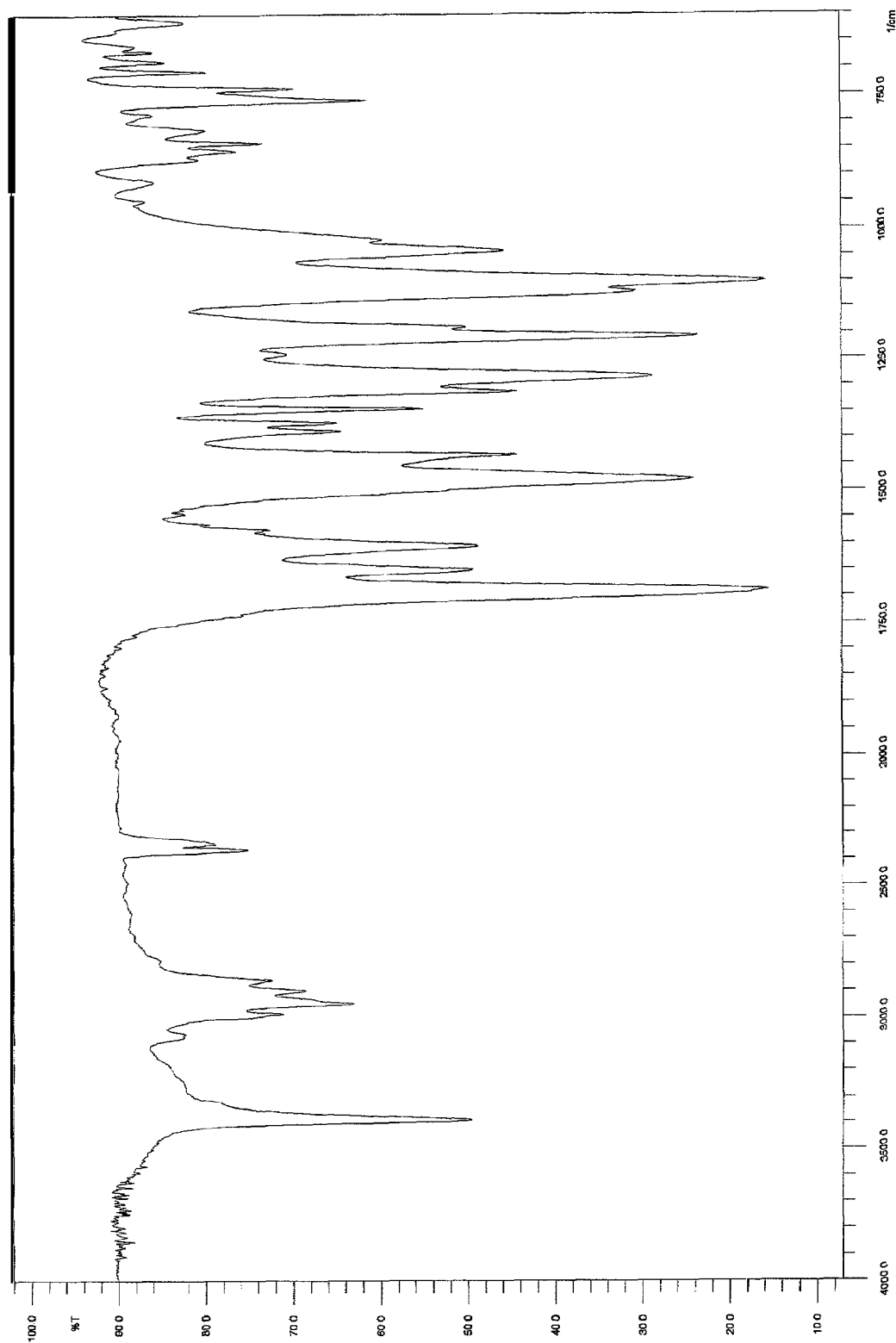
FIG. 2 shows an IR spectrum of crystalline amlodipine free base (Form I) of example 1.
Figure 3:
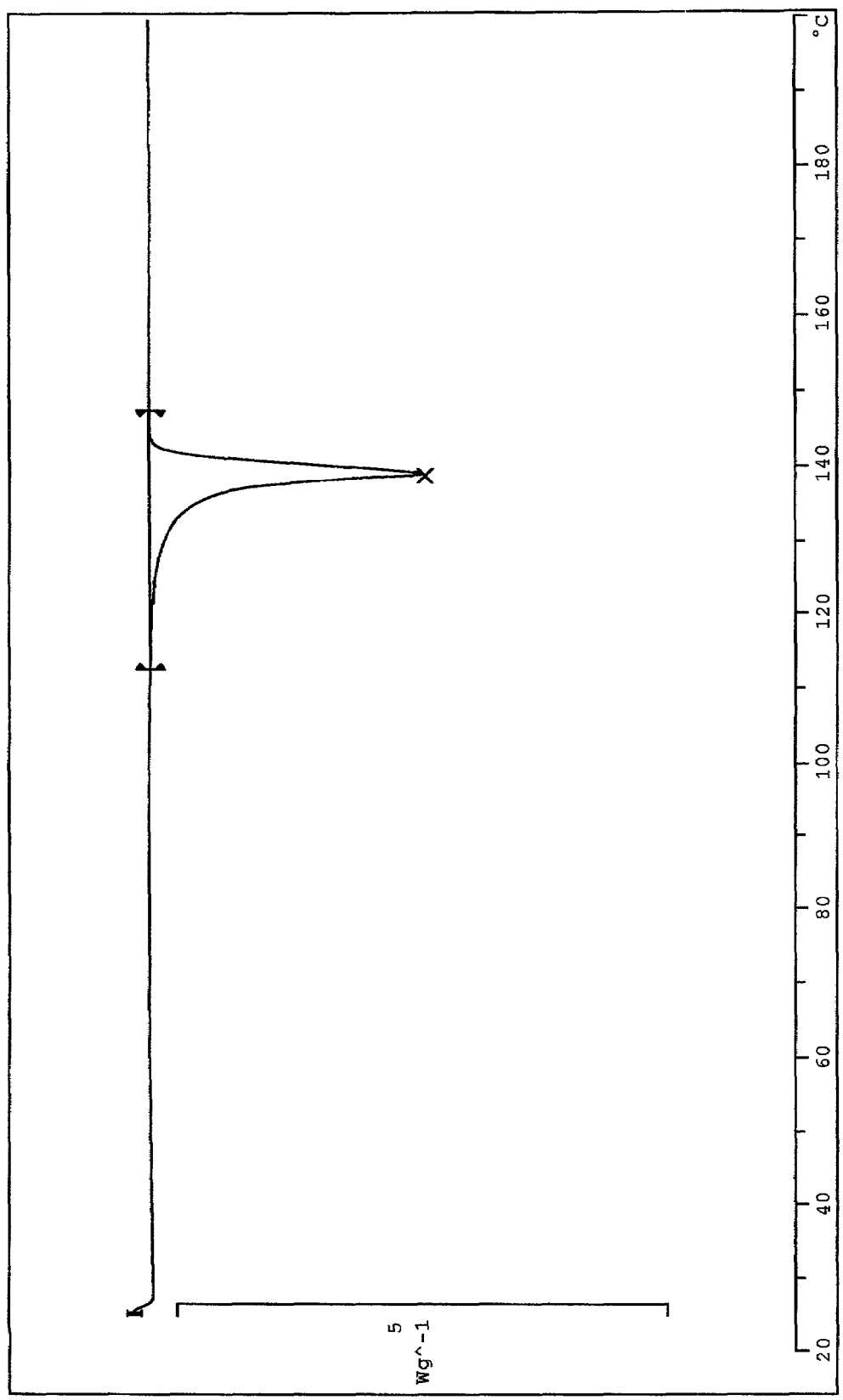
FIG. 3 shows a DSC curve of crystalline amlodipine free base (Form I) of example 1.
Figure 4:
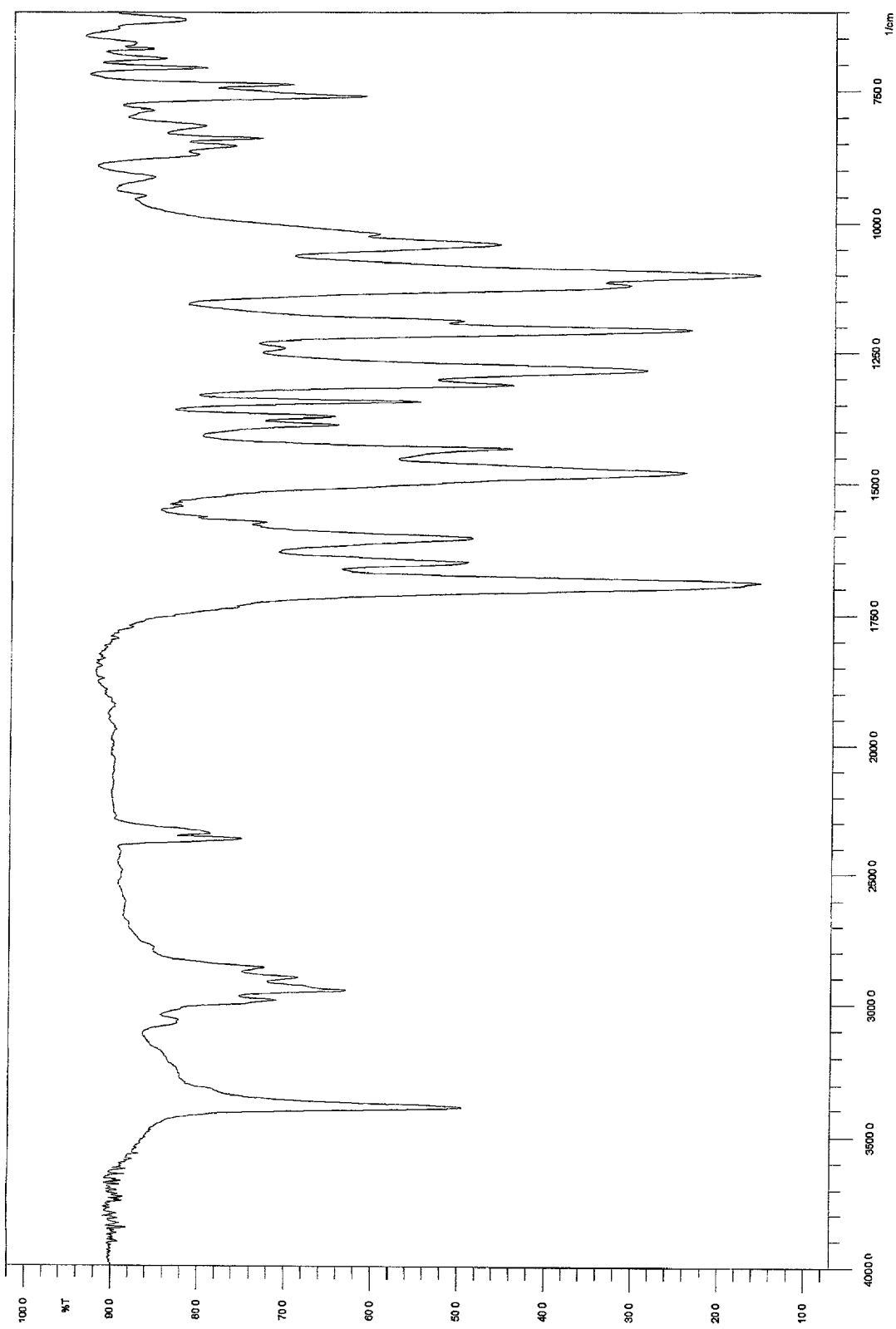
Figure 5:
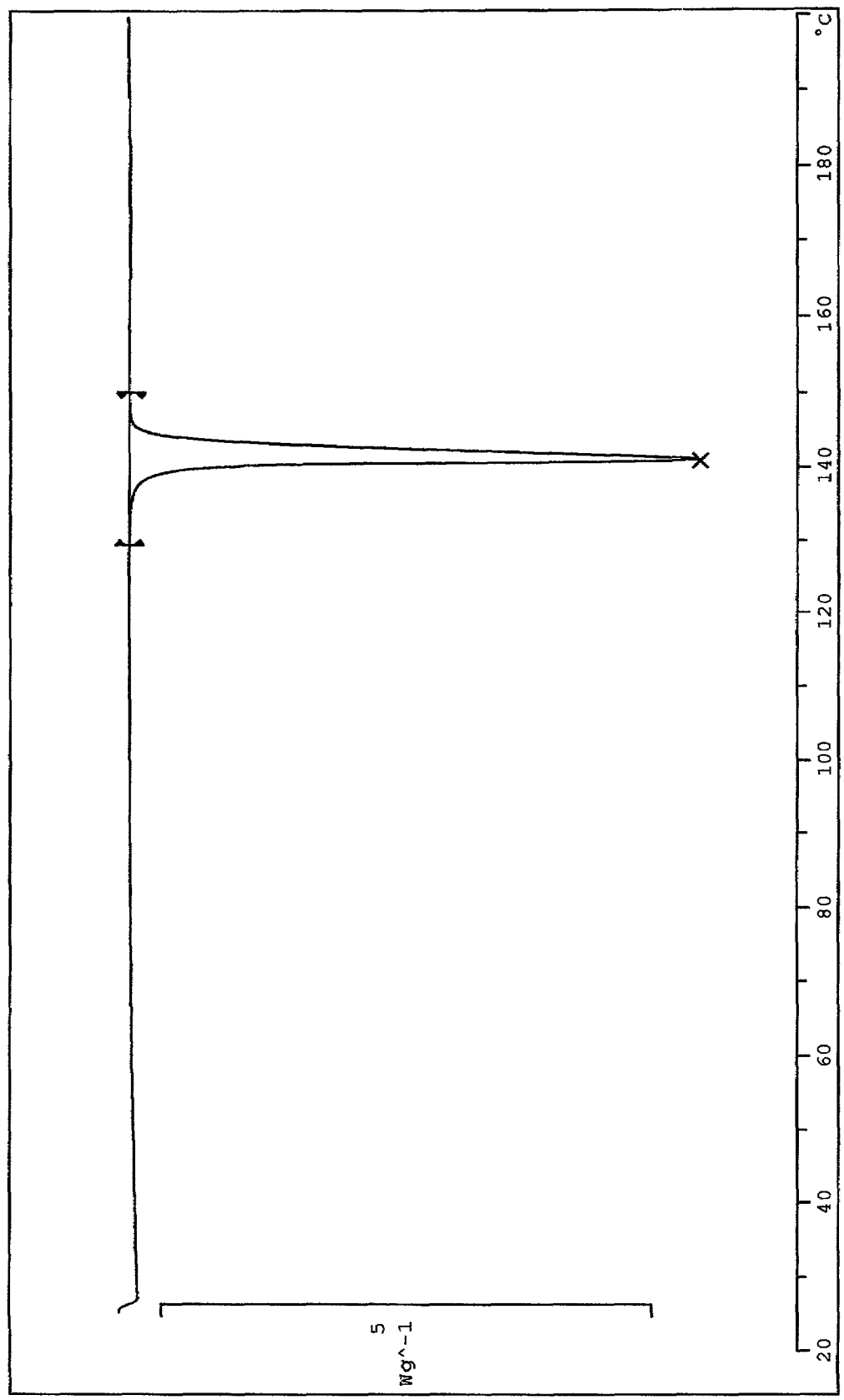
Figure 6:
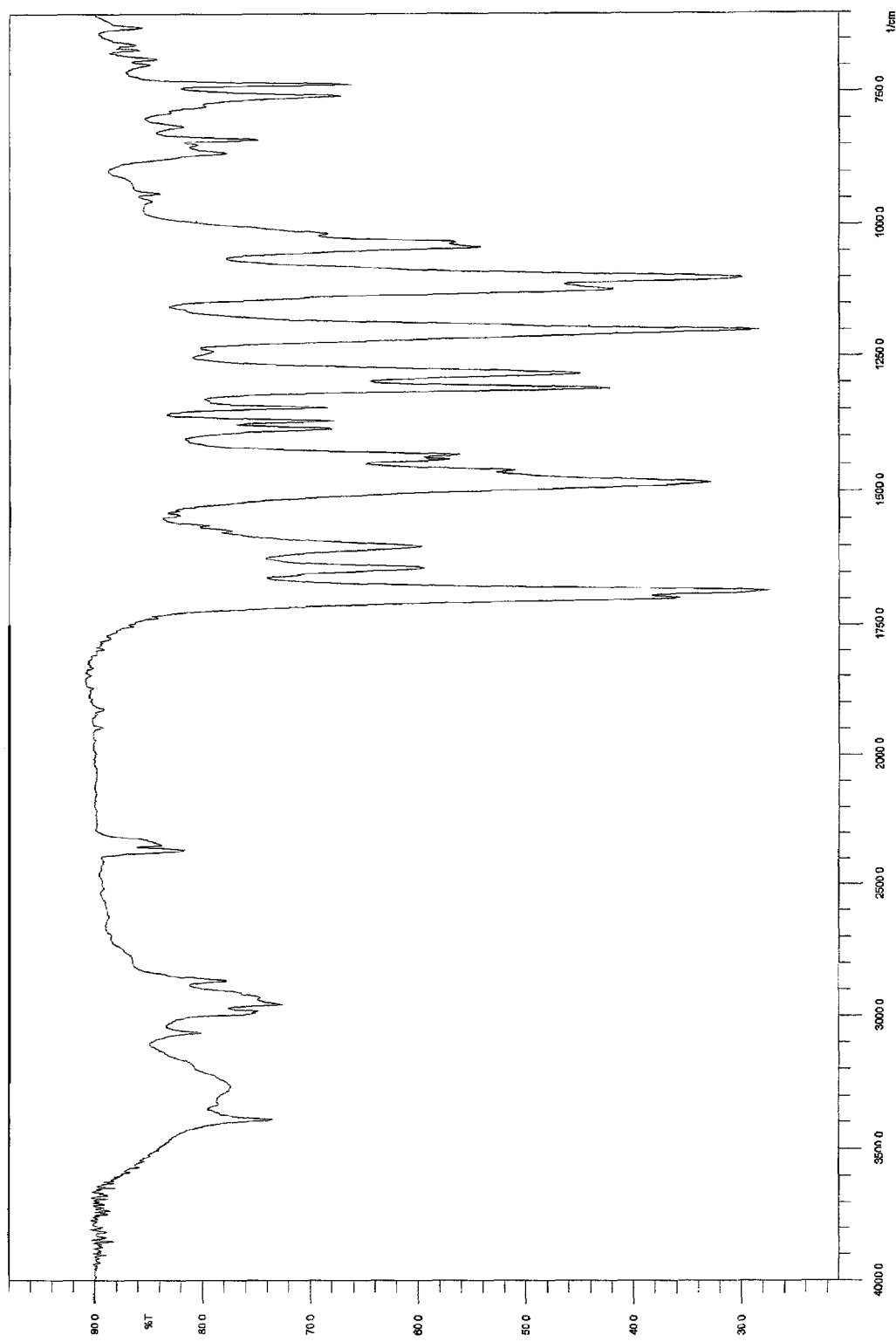
Figure 7:
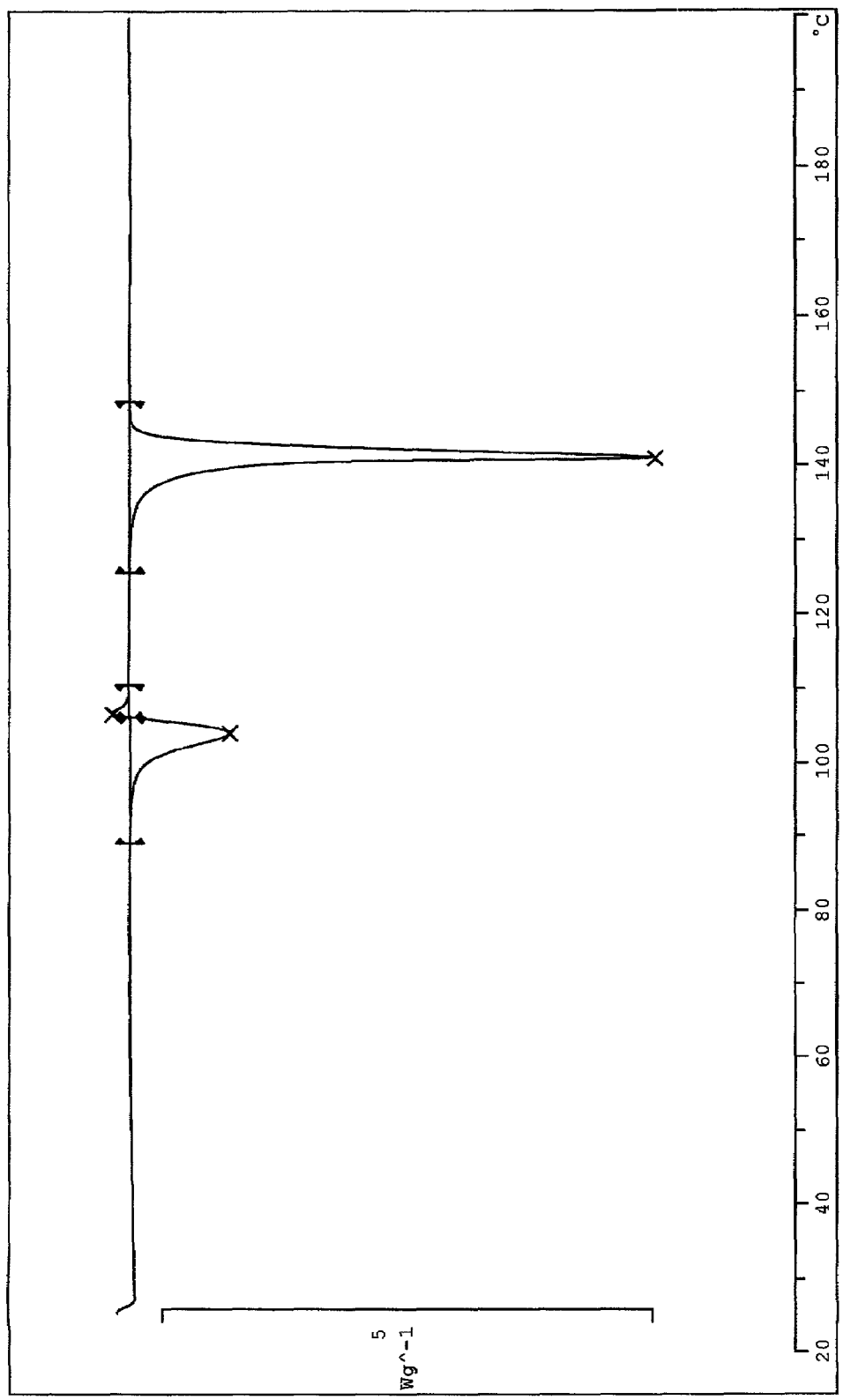
Figure 8:
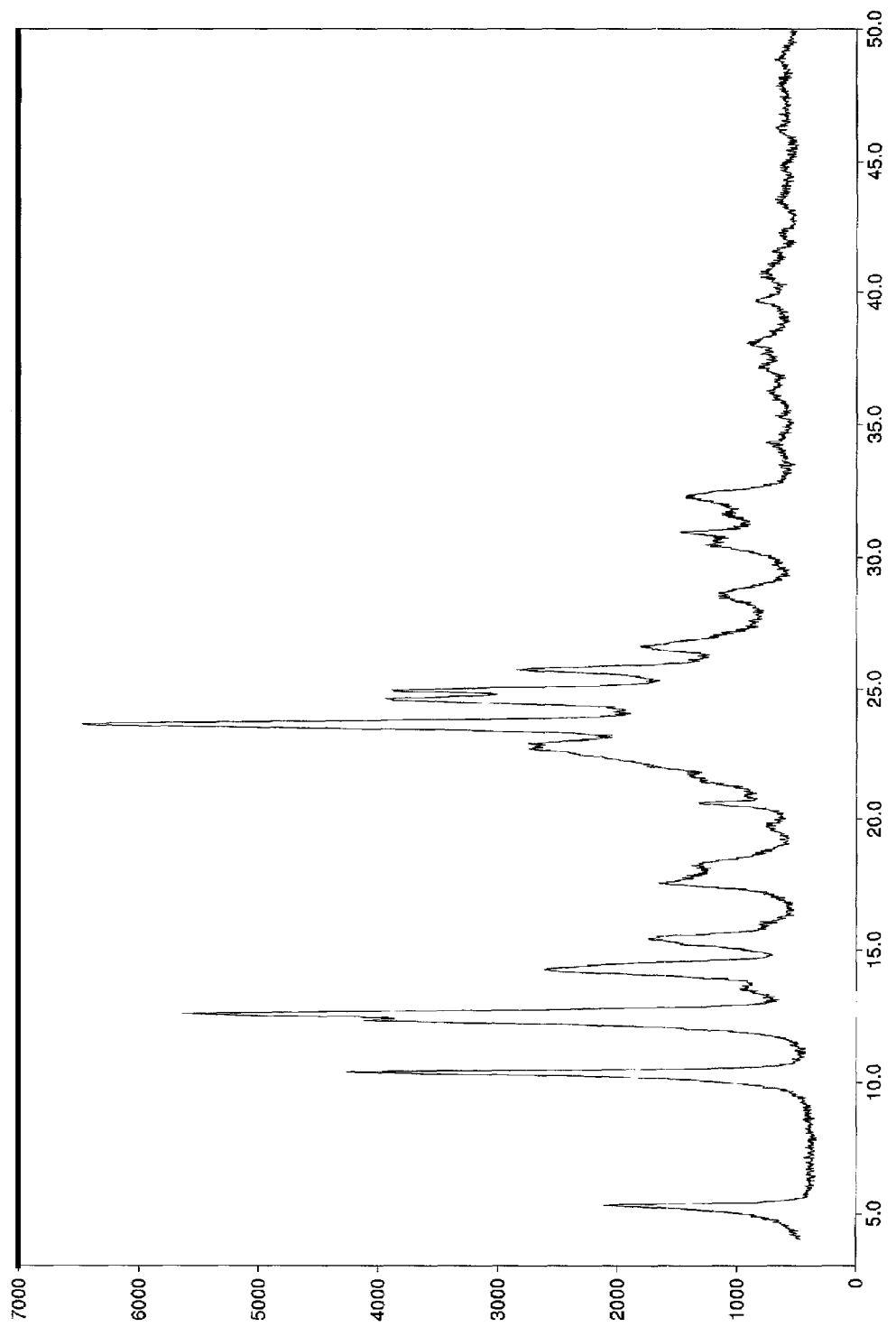
FIG. 8 shows a powder x-ray diffractogram of crystalline amlodipine free base (form II) of example 5b.

The amlodipine free base can be of any form including crystalline form I, crystalline form II or amorphous. The Form I is characterized by a powder x-ray diffraction pattern as shown in FIG. 1, an IR spectrum as shown on FIG. 2 or 4 and by a single melting endotherm on DSC curve with onset at about 140 C. as shown in FIGS. 3 and 5. This form corresponds to the material described by McDaid and Deasy. Form II is a new form and is characterized by a distinctive powder x-ray diffraction pattern as shown in FIG. 8, an IR spectrum as shown in FIG. 6 and by a DSC curve characterized by a transition endotherm or endo/exotherm at a temperature of about 100° C. and a melting endotherm at about 140° C. as shown in FIG. 7. Although it is possible to convert Form II into Form I by applying sufficiently high temperatures, generally over 100 C., Form II is generally stable at ambient conditions and even at moderately elevated temperatures. For instance, the Form II is stable after 1 month standing at 60° C. Accordingly, Form II is thus useful in manufacturing of pharmaceutical final forms. The amlodipine free base in the tablet of the present invention can be of a single type or can be a mixture. For example, a mixture of crystalline Forms I and II.

To reduce the stickiness of the tablets, it is generally desired to control the amlodipine free base size and/or the excipients used. Specifically, it is preferred that the amlodipine free base be incorporated into the tablet composition in the form of particulates having an average particle size of at least 100 microns, preferably 150 to 350 microns, more preferably 200 to 300 microns. The particulates are generally crystals of amlodipine free base, although non-crystalline forms are also included. The moisture in the tablet is preferably limited in order to reduce stickiness. The preferred excipients are calcium phosphate and microcrystalline cellulose as described above.

The amount of amlodipine free base is not particularly limited and includes any amount that provides a pharmaceutical effect. In particular, amlodipine free base can be used to treat or prevent hypertension congestive heart failure or angina by administering an effective amount to a patient in need thereof. The specific form of angina is not particularly limited and specifically includes chronic stable angina pectoris and vasospastic angina (Prinzmetal's angina). The "patients" intended to be treated include human and non-human animals, especially human and non-human mammals. Generally the amount of amlodipine free base in a unit dose is from 1 to 100 mg, more typically from 1 to 25 mg, and preferably about 1, 1.25, 2.5, 5 or 10 mg. In relative terms, the amount of amlodipine free base in the composition may be preferably between 2 and 10%.

The amlodipine free base used in the tablet of the present invention can be made by any convenient means. Preferably, the free base is formed and isolated by a process that comprises deprotecting an N-protected amlodipine with a deprotecting agent to form amlodipine free base; precipitating said amlodipine free base from a solution; and isolating said precipitated amlodipine free base in solid state form. An N-protected amlodipine is an amlodipine compound wherein the terminal amino group is protected as shown in formula (2):

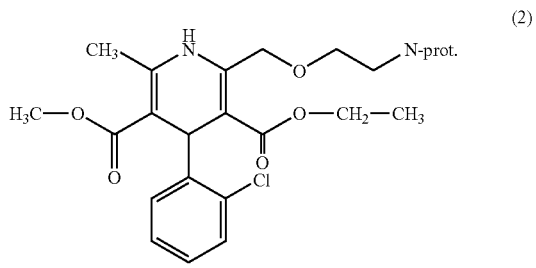

(2)

wherein N-prot means an amino group protected by a cleavable protective group, such as by a benzyl group or a trityl group, or masked within a group convertible to amino group, such as a phthalimido group or an azido group. In a preferred embodiment, the 5 protected amlodipine is a phthalimido-protected amlodipine compound of formula (2a):

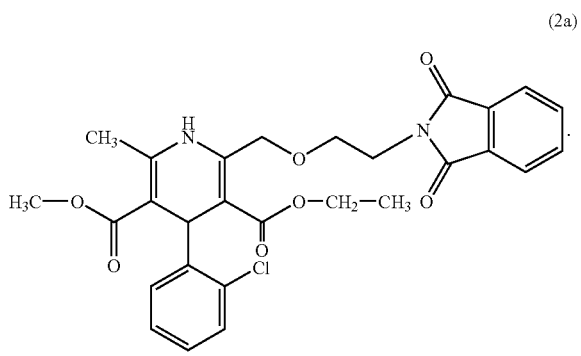

(2a)

This protected amlodipine is frequently referred to hereinafter as phthalodipine.

According to the invention, amlodipine free base may be prepared in the solid state by a suitable elaboration of the reaction mixture obtained after the last synthetic step leading to amlodipine; namely the step comprising deprotection of amlodipine precursor of the above formula (2). Suitable deprotecting agents are well known in the art and the selection thereof is dependent on the protecting group being employed. The amlodipine free base is obtained without the need to form, and particularly to isolate, an amlodipine salt. The process is characterized in that no acidic agent or medium is employed for the deprotection nor for the elaboration purposes; i.e. the amlodipine free base formed by deprotection is the free base that is precipitated without the intermediate step of forming an amlodipine salt.

The process of the present invention requires "precipitating" amlodipine free base from a solution. Precipitation is a well known phenomenon whereby a solid phase separates from a solution. It is an advantage of a precipitation that the solid phase comprising the desired product may be separated from the liquid phase comprising the solvent and soluble co-products, i.e. side products or impurities. Precipitation is thus also a tool how to get rid of at least some impurities from the product. This is not possible if a solid product is obtained from a solution by simple evaporation of the solvent. Thus, for purposes of the present invention precipitation does not include evaporating off all the solvent in a solution to leave a residue. The precipitation is preferably a crystallization, although it is not limited thereto. Precipitation that involves reducing the temperature of the solution generally leads to crystallization while precipitation that involves a change in pH may lead to a more classic precipitation of the solid in either crystalline or non-crystalline form. The solution can be formed directly by the deprotection step or it can be a different solution such as one formed by an extraction process. The solution can be aqueous, non-aqueous, or a mixture of solvents. In general, an aqueous solvent leads to the formation of small particle sizes. The purification step described hereinafter can be used to obtain amlodipine free base particles of a larger size as desired.

Isolation of the precipitated solid form of amlodipine free base can be by any suitable or known technique for separating a solid phase from a liquid phase, i.e., a solvent or solution. Preferably the isolation step uses filtration.

The invention will be described with respect to its preferred embodiment wherein phthalodipine of formula (2a) is used as the N-protected amlodipine compound. According to EP 89167, phthalodipine is deprotected either by ethanolic methylamine, ethanolic hydrazine hydrate or by KOH in water/tetrahydrofuran mixture. These techniques are suitable for the process of our invention, however they are rather uneconomical. In a more advantageous mode, the deprotection is performed by treatment of phthalodipine with an aqueous solution of methylamine. It is the advantage of aqueous solution of methylamine that amlodipine free base simply separates out from the reaction mixture and may be simply isolated in solid state by filtration. The co-product of deprotection reaction (N-methylphthalamide) remains in the aqueous solution.

The reaction with aqueous methylamine may be performed at a temperature from the ambient to approx. 60° C., preferably at 30-50° C. The course of reaction may be monitored by any suitable analytical technique allowing for separation of the starting material and the product, e.g. by HPLC. The product may be separated by filtration at 5-25° C., preferably at ambient temperature.

In an alternate mode, the reaction mixture comprising amlodipine free base may be elaborated by extraction of amlodipine from the alkaline aqueous solution by an water immiscible organic solvent, e.g. toluene. The temperature of extraction is essentially ambient. Concentration of the extraction solution allows for precipitation of crude amlodipine free base in solid state. A contrasolvent (e.g. hexane) may be also added to the extraction solution, particularly to the concentrated solution, to facilitate precipitation of amlodipine free base in solid state.

Crude solid amlodipine free base may be further purified by various techniques. It should be noted that the meaning "crude solid" amlodipine is not limited only to the solid amplodipine base prepared by the above method of our invention but it embraces any solid amlodipine base that has to be further purified. Purification is used herein in a broad sense to include improving crystal size, i.e. removing small crystals in favor of larger crystals, as well as reducing the level of contaminants in the amlodipine free base. In particular, precipitation from aqueous solutions generally produces amlodipine free base as fine particles. Purifying through a crystallization purification step can be used to obtain amlodipine free base crystals having a larger, more desirable particle size.

In a first purification method, amlodipine free base is crystallized from a solution based on a suitable nonaqueous solvent, sometimes hereinafter referred to as a "purification solvent." Preferably, the dissolution of amlodipine in the solvent is carried out under elevated temperature that may comprise even the boiling temperature of the purification solvent. If desired, the obtained solution may be further purified by conventional adsorption techniques, e.g. by treatment with activated charcoal or silica gel, prior crystallization. The crystallization from solution may be performed by various ways:

- by spontaneous or forced cooling the solution of amlodipine free base
- by adding at least partly miscible contrasolvent to a solution of amlodipine free base (under stirring or under diffusion), optionally in combination with spontaneous or forced cooling
- by evaporation of a part of the solvent, optionally in combination with any of the preceded techniques Suitable solvents comprise aliphatic C1-C4 alcohols such as methanol or ethanol, chlorinated C1-C4 hydrocarbons such as chloroform, alkyl esters of aliphatic acids such as ethyl acetate, nitriles of aliphatic acids such as acetonitrile, aromatic hydrocarbons such as toluene, C1-C6 ketones such as acetone, and mixtures thereof. Suitable contrasolvents may be either more polar than the solvent; an example is water, or be less polar than the solvent; an example is hexane or heptane.

In another purification method, crude amlodipine free base is dissolved in a suitable water immiscible or sparingly miscible purification solvent, e.g. toluene, the toluene solution is extracted by an aqueous acid to provide an aqueous solution of amlodipine salt, which is then neutralized by a base, e.g. an alkali or an amine. The formed amlodipine base may precipitate from the aqueous solution and may be separated, or may be extracted back into an organic solvent immiscible or sparingly miscible with water which is then cooled, concentrated or mixed with a contrasolvent, whereby purified amlodipine free base precipitates from the solution. The nature of the acid should be preferably so selected that the formed amlodipine salt is soluble in water. Suitable acid is hydrochloric acid.

Amlodipine free base in a solid form can be prepared also by freeze drying of a solution thereof, e.g. a solution in ethanol-water (2:1).

By any of the above production or purification methods, except when working under conditions that will be discussed below, amlodipine free base has been obtained in crystalline Form I.

Under certain conditions, a novel polymorphic form of solid-state amlodipine free base (Form II) can be prepared from amlodipine free base solutions. In general, the conditions require crystallization to begin at low temperatures and typically with rapid cooling to avoid the formation of Form I nuclei. For instance, Form II is formed if a solution of amlodipine free base in a non-aqueous solvent, e.g. in toluene, is treated by a contrasolvent, e.g. by hexane, cyclohexane or heptane, at temperatures below 5° C. The "solution of amlodipine free base in a non-aqueous solvent" includes the crude solution, e.g. toluene solution, obtained after the above deprotection step. Adding a contrasolvent embraces putting a contrasolvent into the cooled or cooling amlodipine free base solution or applying the amlodipine free base solution to a cooled contrasolvent. Generally, the use of a contrasolvent allows for a higher crystallization temperature to be used in forming form II.

In an alternative process, Form II may be formed by a precipitation after forced cooling a solution of amlodipine free base in a suitable crystallization solvent, e.g. ethyl acetate, wherein the precipitation starts at the temperature below 5° C., more preferably below −5° C., and more usually at −10° C. or below including −20° C. and below.

It should be noted that amlodipine free base, particularly crystalline amlodipine free base Form II and purified amlodipine free base described above, may also be used as an intermediate in the production of amlodipine acid addition salts. In an advantageous mode, amlodipine base purified by methods of the invention is reacted with a pharmaceutically acceptable acid to form an amlodipine salt that exhibits a desired degree of purity, e.g. pharmaceutical purity, without a need of further purification.

Amlodipine salts may be prepared by e.g. treating the solution or suspension of amlodipine base in a suitable solvent with an equivalent amount of an acid and isolation of the formed salt from the reaction mixture. Amlodipine salts preparable by this method preferably include, but are not limited to, salts with pharmaceutically acceptable acids; examples are amlodipine maleate, fumarate, hydrogenmaleate, besylate, besylate monohydrate, besylate dihydrate, hydrochloride, mesylate, mesylate monohydrate, hydrobromide, citrate and tartrate.

Suitable process for making amlodipine free base tablet may comprise any conventional process. The compositions of this invention may be formulated by conventional methods of admixture such as blending, filling and compressing, by means of wet granulation, dry granulation or direct compression. The later process is the most advantageous and preferred one and may be applied to the tablet composition of the invention in industrial scale.

While the present invention is directed primarily to tablets, a capsule dosage form can also be prepared from amlodipine free base. The capsule compositions may comprise essentially the same excipients as for tablet compositions. Advantageous inert carrier is microcrystalline cellulose without calcium phosphate.

Amlodipine free base may be also used in medical applications in combination with other antihypertensive and/or antianginal agents, for instance with ACE-inhibitors such as benazepril. The combination may be in a form of single combination preparation, e.g. a capsule containing amlodipine free base and benazepril hydrochloride, or by separate administration of drugs containing the above agents. Amlodipine free base may be also used in combination with various cholesterol-lowering agents such as lovastatin, simvastatin or atorvastatin.

Amlodipine free base may be used in the management of the following disorders:

hypertension
chronic stable angina pectoris
vasospastic angina (Prinzmetal's angina)
Congestive heart failure These disorders are hereinafter referred to as "the Disorders". Accordingly, the present invention further provides a method for treating and/or preventing any one or more of the Disorders by administering an effective and/or prophylactic amount of amlodipine free base within a composition of the invention to a sufferer in need thereof. An effective amount is known in the art. For example, in humans, an effective amount is typically between 1 and 100 mg of amlodipine free base. A unit dose as previously described is normally taken from 1 to 3 times daily, preferably once a day. In practice, the physician will determine the actual dosage and administration regimen which will be the most suitable for the individual patient.

The present invention also provides the use of the composition of the invention in the manufacture of a medicament for treating and/or preventing any one or more of the Disorders.

The following examples illustrate the invention but should not be construed as limiting the invention thereto.

Reference Example 1 Based on McDaid and Deasy

| | |
|---|---|
| 1.15 g | of amlodipine besylate was dissolved in |
| 250 ml | of water at 50° C.-55° C. |
| 2.2 ml | of a 1 M NaOH solution was added. The mixture was put at 3° C.-5° C. and stirred at this temperature for 1 hours. The solid was filtered off and washed with |
| 2*5 ml | of water and dried in a vacuum oven. |
| 0.73 g | of a solid was obtained. |
| | Yield: 0.73 g (88%) |
| | NMR: corresponds to amlodipine free base |
| | DSC: Corresponds to amlodipine free base Form I |

Reference Example 2 Based on McDaid and Deasy

| | |
|---|---|
| 1.5 g | of amlodipine besylate was dissolved in |
| 30 ml | of methanol. |
| 3.1 ml | of a 1 M NaOH solution was added. |
| 40 ml | of diethyl ether was added. No separation of layers observed. |
| 10 ml | of water added. Layers separated and organic layer dried over $Na_2SO_4$. The mixture was evaporated to dryness and the obtained solid dried in a vacuum oven. |
| 0.85 g | of a solid was obtained. |
| | Yield: 0.85 g (78%) |
| | NMR: corresponds to amlodipine free base |
| | DSC: corresponds to amlodipine free base Form I |

Reference Example 3

| | |
|---|---|
| 6 kg | of amlodipine beyslate was suspended in |
| 12 l | of 2-propanol. Stirred at 200 RPM for 15 minutes. |
| 10.6 l | of NaOH 1 M in water was added. No exothermic effect was observed. Stirred at 200 RPM for 1 hour. |
| 20 l | of water was added in 10 minutes, seeding crystals were added. |
| 4 l | of water was added, small exothermic effect was observed due to crystallisation. Stirring rate was set to 150 RPM and stirred for 1 hour at 20° C. The reaction mixture was cooled to 5° C. in 2 hours and stirred at 5° C. for 30 minutes. The solid was filtered off and washed with |
| 2*5 l | of water. The solid was dried in a vacuum oven at 40° C. for 4 days. |

Yield 4.05 kg (93.5%) of slightly yellow crystals, average particle size about 230 microns.
purity 99.7%
NMR: corresponds to amlodipine free base
DSC and IR showed form I
XRPD is shown in FIG. 1.

EXAMPLE 1

Synthesis of Amlodipine Free Base

| | |
|---|---|
| 250 ml | of 40% methylamine in water and |
| 31.5 g | of phthalodipine were stirred at 40° C.-45° C. for 16 hours. |
| 460 ml | of toluene was added and the mixture was stirred for 30 minutes. The layers were separated and the organic layer washed with |
| 150 ml | of water. The layers were separated and the organic layer evaporated to dryness. The obtained solid was dried at 40° C. in a vacuum oven. |
| 21.6 g | of a solid was obtained. |

Yield: 21.6 g (92%)
HPLC: 98.8 area %
Mp: 136° C.-139° C. (uncorrected)
IR: corresponds to Form I as shown in FIG. 2.
DSC: corresponds to form I as shown in FIG. 3.

EXAMPLE 2

Synthesis of Amlodipine Free Base

| | |
|---|---|
| 100 ml | of 40% methylamine in water and |
| 12.6 g | of phthalodipine were stirred at 40° C.-45° C. for 16 hours. |
| 150 ml | of toluene was added and the mixture was stirred for 30 minutes. The layers were separated and the organic layer washed with |
| 50 ml | of water. The mixture was reduced to approximately 20 ml and cooled, under stirring, on an ice bath. A solid started to precipitate which was filtered off and washed with |
| 5 ml | of toluene. The solid product was dried in vacuum oven. |

HPLC: 98.8 area %
NMR: corresponds to amlodipine base
DSC: corresponds to amlodipine base Form I

EXAMPLE 3

Synthesis of Amlodipine Free Base

| | |
|---|---|
| 100 ml | of 40% methylamine in water and |
| 12.6 g | of phthalodipine were stirred at 40° C.-45° C. for 16 hours. The mixture was filtered and the obtained solid was washed with |
| 2 × 10 ml | of water. The solid was dried in a vacuum oven. |

Yield: 6 g (64%)
HPLC: 98.8 area %
NMR: corresponds to amlodipine base
DSC: corresponds to amlodipine base Form I

EXAMPLE 4a

Crystallization of Amlodipine Base to Form Form I

| | |
|---|---|
| 6.5 g | of the crude amlodipine free base from Example 1 was dissolved in |
| 60 ml | of boiling ethanol. |
| 120 ml | of water was added and the mixture was left to cool to room temperature. During cooling a solid starts to precipitate. The mixture was cooled on an ice bath for 1 hour. The solid was filtered off and washed with |
| 10 ml | of water. The solid was dried in a vacuum oven at 40° C. |
| 5.8 g | of a solid was obtained. |

Yield: 5.8 g (89%)
HPLC: 99.3 area %
Mp: 140° C.-141° C. (uncorrected)
IR: corresponds to Form I as shown in FIG. 4
DSC: corresponds to Form I as shown in FIG. 5.

EXAMPLE 4b

| | |
|---|---|
| 2.0 g | of amlodipine free base was dissolved in |
| 5 ml | of ethyl acetate by heating at reflux, and filtered over hyflo to obtain a clear solution. This warm solution was added dropwise to |
| 100 ml | of heptane under vigorous stirring. Amlodipine precipitated from the mixture and was isolated by filtration. The crystals (fine powder) were dried in vacuum at room temperature. |

EXAMPLE 5a

Crystallization of Amlodipine Base to Form Form II

| | |
|---|---|
| 6.5 g | of amlodipine free base from Example 1 was dissolved in |
| 25 ml | of boiling toluene. This mixture was slowly added, in 15 minutes, to a 0°-3° C. |
| 300 ml | of n-hexane solution under stirring. During addition the temperature of the n-hexane solution was kept below 3° C. The solid was filtered off and dried under vacuum at ambient temperature. |
| 6.0 g | of a white solid was obtained. |

Yield: 6.0 g (92%)
HPLC: 99.3 area %
IR: corresponds to Form II as shown in FIG. 6.
Mp: 138° C.-140° C. (uncorrected)
DSC: 100.12° C. onset and 140.39° C. onset as shown in FIG. 7.

EXAMPLE 5b

| | |
|---|---|
| 5.0 g | of amlodipine free base was dissolved in |
| 10 ml | of ethyl acetate by heating at reflux. Immediately after a clear solution was obtained, the hot mixture was forced to cool to −78° C. (dry-ice/acetone). No crystallisation occurred. However, out of the dry-ice bath, suddenly the solution solidified. The crystals (powder-like) were isolated by filtration, and dried in vacuum at room temperature. |

IR: corresponds to Form II

EXAMPLE 5c

| | |
|---|---|
| 2.0 g | of amlodipine free base was dissolved in |
| 6 ml | of ethyl acetate by heating at reflux. The hot solution was filtered over hyflo, to obtain a clear solution, and added dropwise to |
| 100 ml | of heptane under vigorous stirring at −78° C. The temperature of the heptane layer was kept below −70° C. The precipitate was collected by filtration and dried under vacuum at room temperature overnight. |

IR: corresponds to Form II.

EXAMPLE 5d

| | |
|---|---|
| 2.5 g | of amlodipine free base was dissolved in |
| 7 ml | of ethyl acetate by heating at reflux. The hot solution was filtered over hyflo, and added dropwise to a ice-cooled (0° C.) layer of |
| 100 ml | of heptane under vigorous stirring. The temperature of the heptane layer was kept between 0-1° C. The precipitate was isolated by filtration and dried under vacuum at room temperature overnight. |

IR: corresponds to Form II

EXAMPLE 5e

| | |
|---|---|
| 2.0 g | of amlodipine free base was dissolved in |
| 10 ml | of toluene by heating to reflux. The hot solution was filtered over hyflo, and added dropwise to a pre-cooled (0° C.) layer of |
| 100 ml | of heptane under vigorous stirring. The temperature of the heptane layer was kept between 0-1° C. The precipitate was isolated by filtration and dried under vacuum at room temperature overnight. |

IR: corresponds to Form II

EXAMPLE 6a

Synthesis of Amlodipine Free Base Form II

| | |
|---|---|
| 100 ml | of 40% methylamine in water and |
| 12.6 g | of phthalodipine were stirred at 40° C.-45° C. for 16 hours. |
| 150 ml | of toluene was added and the mixture was stirred for 30 minutes. The layers were separated and the organic layer washed with |
| 50 ml | of water. The mixture was reduced to approximately 75 ml and cooled on an ice-salt bath to approximately −10° C. A solid was formed which was filtered off and washed with |

-continued

| | |
|---|---|
| 5 ml | of toluene. The solid product was dried in vacuum oven. |

Yield: g (92%)
HPLC: (98.8 area %)
NMR: corresponds to amlodipine free base
DSC: corresponds to amlodipine base Form II

EXAMPLE 6b

Synthesis of Amlodipine Free Base Form II

| | |
|---|---|
| 100 ml | of 40% methylamine in water and |
| 12.6 g | of phthalodipine FB.ADP.010710.01 were stirred at 40° C.-45° C. for 16 hours. |
| 150 ml | of toluene was added and the mixture was stirred for 30 minutes. The layers were separated and the organic layer washed with |
| 50 ml | of water. The organic layer was reduced to 75 ml and cooled to −20° C. |
| 75 ml | of n-heptane was added. A solid started to precipitate which was filtered off. The solid was washed with |
| 2*5 ml | of n-heptane and dried in a vacuum oven |
| 7.9 g | of a solid was obtained. |

Yield: 7.9 g (85%)
HPLC: (98.8 area %)
NMR: corresponds to amlodipine free base
IR: corresponds to Form II
DSC: corresponds to Form II

EXAMPLE 7

Conversion of Amlodipine base Form II to Form I

| | |
|---|---|
| 1 g | of amlodipine base Form II was heated at 115° C. for 4 hours. The compound turned slightly yellow. 0.9 g of a solid was retrieved. |

IR: corresponds to amlodipine free base
DSC: corresponds to form I

EXAMPLE 8

Purification of Amlodipine Base Via a Salt

| | |
|---|---|
| 2.3 g | of crude amlodipine base was dissolved in |
| 50 ml | of toluene. |
| 150 ml | of a 0.05 M HCl solution was added and the mixture was vigorously shaken. The layers were separated and to the aqueous layer was added |
| 10 ml | of a 1 M NaOH solution. A solid started to form and the mixture was stirred for 45 minutes at 3° C.-5° C. The solid was filtered off and washed with |
| 2 × 5 ml | of water. The solid was dried in a vacuum oven. |
| 1.65 g | of a solid was obtained. |

Yield: 1.65 g (72%)

NMR: corresponds to amlodipine base
DSC: corresponds to amlodipine base Form I

EXAMPLE 9

Stickiness Comparison

Tablets with the following composition were made on a EKO Excenter Press (Korsch):

Amlodipine besylate tablets 47.5% Microcrystalline Cellulose (Avicell PH 112; FMC)

47.5% Calcium sulphate dihydrate (Compactrol; Penwest Pharmaceuticals Co)

5.0% Amlodipine besylate

Amlodipine free base tablets 48.2% Microcrystalline Cellulose (Avicell PH 112; FMC)

48.2% Calcium sulphate dihydrate (Compactrol; Penwest Pharmaceuticals Co)

3.67% Amlodipine base (Ref. Ex. 3)

Tablet properties:

| | |
|---|---|
| Punch diameter: | 20 mm |
| Tablet weight: | 400 mg |
| Hardness: | appr. 200 N |

After 50 tablets, the tablet material was extracted from the punches using methanol and an ultrasonic bath. This procedure was repeated for runs of 100, 150, 200, 250 and 300 tablets. The extracts together with Amlodipine calibration samples were measured spectrometrically. The amount of Amlodipine in the samples was calculated from the calibration curve and the total amount of Amlodipine extracted from both the upper and lower punch was plotted against the amount of tablets made. An average value for stickiness was calculated from the slope of the regression line by forcing the y-intercept of the line through zero.

| | |
|---|---|
| Average residue (stickiness) Amlodipine base: | 0.55 µg ADP.cm$^{-2}$.tablet$^{-1}$ |
| Average residue (stickiness) Amlodipine besylate: | 1.16 µg ADP.cm$^{-2}$.tablet$^{-1}$ |

EXAMPLE 10

Pharmaceutical Tablet Comprising Amlodipine Free Base a) Tablet composition with calcium hydrogen phosphate/microcrystalline cellulose

| Batch number | A | B | C | D | E | F |
|---|---|---|---|---|---|---|
| Amlodipine base (from Ref. Ex. 3) | 2.5 mg | 10 mg | — | — | 2.5 mg | 10 mg |
| Amlodipine base milled (fro Re. Ex. 3) | — | — | 2.5 mg | 10 mg | — | — |
| Calcium hydrogenphosphate anhydroous | 31.5 mg | 126.0 mg | 31.5 mg | 126.0 mg | 31.5 mg | 126.0 mg |
| Microcrystalline cellulose | 62.05 mg | 248.1 mg | 62.05 mg | 248.1 mg | 62.05 mg | 248.1 mg |
| Sodium starch glycollate | 2.0 mg | 8.0 mg | 2.0 mg | 8.0 mg | 2.0 mg | 8.0 mg |
| Magnesium Stearate | 1.0 mg | 4.0 mg | 1.0 mg | 4.0 mg | 1.0 mg | 4.0 mg |
| Total | 99.05 mg | 396.1 mg | 99.05 mg | 396.1 mg | 99.05 mg | 396.1 mg |

Batches amlodipine base A, B, E, and F were manufactured as follows:

The amlodipine base was sieved through a 500 μm screen.
The other excipients have been sieved through a 850 μm screen.
All excipients except magnesium stearate have been mixed in a free fall mixer for 15 minutes at about 25 rpm.
Magnesium stearate was added and the powder blend was mixed for another 5 minutes at about 25 rpm.
2.5 mg and 10 mg tablets have been compressed using a Korsch EKO excenter press.

Batches amlodipine C and D were manufactured as follows:

The AMLODIPINE base was milled.
The other excipients have been sieved through a 850 μm screen.
All excipients except magnesium stearate have been mixed in a free fall mixer for 15 minutes at about 25 rpm.
Magnesium stearate was added and the powder blend was mixed for another 5 minutes at about 25 rpm.
2.5 mg and 10 mg tablets have been compressed using a Korsch EKO excenter press.

No problems were encountered with production of the above tablets.

b) Tablet composition based on microcrystalline cellulose

| Batch number | G | H |
|---|---|---|
| Amlodipine base (from ref. Ex. 3) | 2.5 mg | 10 mg |
| Microcrystalline cellulose | 75.55 mg | 302.1 mg |
| Predried potato starch | 20.0 mg | 80.0 mg |
| Magnesium Stearate | 0.5 mg | 2.0 mg |
| Talc | 0.5 mg | 2.0 mg |
| Total | 99.05 mg | 396.1 mg |

Manufacturing process:

The amlodipine base was sieved through a 500 μm screen.
The other excipients have been sieved through a 850 μm screen.
All excipients except magnesium stearate and talc have been mixed in a free fall mixer for 15 minutes at about 25 rpm.
Magnesium stearate and talc were added and the powder blend was mixed for another 5 minutes at about 25 rpm.
2.5 mg and 10 mg tablets have been compressed using a Korsch EKO excenter press.

c) Dissolution profiles have been recorded using the paddle apparatus at a rotation speed of 75 RPM and a dissolution medium of 500 ml of 0.01 M hydrochloric acid. The dissolution samples are analysed by UV spectrophotometry at 237 nm. Average dissolution values (in % of the declared amount) are presented in the table.

| Batch | 0 min | 3 min | 6 min | 9 min | 12 min | 15 min | 20 min | 30 min | 45 min | 60 min |
|---|---|---|---|---|---|---|---|---|---|---|
| A | 0 | 83 | 93 | 96 | 97 | 97 | 97 | 97 | 98 | 98 |
| B | 0 | 89 | 97 | 99 | 101 | 101 | 102 | 102 | 103 | 103 |
| G | 0 | 92 | 97 | 98 | 98 | 98 | 99 | 99 | 100 | 100 |
| H | 0 | 86 | 91 | 94 | 95 | 96 | 97 | 99 | 101 | 102 |
| C | 0 | 88 | 95 | 96 | 97 | 97 | 98 | 98 | 98 | 98 |
| D | 0 | 86 | 94 | 96 | 97 | 97 | 98 | 99 | 100 | 100 |

EXAMPLE 11

Amlodipine Free Base Capsules

Composition:

| | |
|---|---|
| Amlodipine base | 5.0 mg |
| Microcrystalline cellulose | 72.6 mg |
| Predried potato starch | 20.0 mg |

|  |  |
| --- | --- |
| -continued | |
| Magnesium stearate | 0.5 mg |
| Total | 98.1 mg |

Procedure:

The amlodipine base was sieved through a 500 μm screen.

The other excipients have been sieved through a 850 μm screen.

All excipients except magnesium stearate have been mixed in a free fall mixer for 15 minutes at about 25 rpm.

Magnesium stearate was added and the powder blend was mixed for another 5 minutes at about 25 rpm.

gelatine capsules have been filled with this powder blend

The invention having been described, it will be readily apparent to those skilled in the art that further changes and modifications in actual implementation of the concepts and embodiments described herein can easily be made or may be learned by practice of the invention, without departing from the spirit and scope of the invention as defined by the following claims.

We claim:

1. A pharmaceutical tablet composition comprising an effective amount of crystalline Form I amlodipine free base and at least one pharmaceutically acceptable excipient; wherein said tablet leaves an average residue of amlodipine on the tablet punch of 0.7 $\mu g \cdot cm^{-2}$ per tablet or less.

2. The composition according to claim 1, wherein said excipient is a calcium phosphate.

3. The composition according to claim 1, wherein said excipient is microcrystalline cellulose.

4. The composition according to claim 3, which further comprises microcrystalline cellulose.

5. The composition according to claim 4, wherein said calcium phosphate is anhydrous calcium hydrogen phosphate.

6. The composition according to claim 1, wherein said tablet contains 1 to 100 mg of said amlodipine free base.

7. A method of treating hypertension, angina, or congestive heart failure, which comprises administering an effective amount of amlodipine free base to a patient in need thereof.

8. The composition according to claim 1, wherein said amlodipine free base was incorporated into said composition in the form of particulates having an avaerage particle size of at least 100 microns.

9. The composition according to claim 8, wherein said average particle size is 150-350 microns.

10. The composition according to claim 9, wherein said average particle size is 200-300 microns.

11. The composition according to claim 8, wherein said excipient is anhydrous calcium hydrogen phosphate.

12. The composition according to claim 9, wherein said excipient is anhydrous calcium hydrogen phosphate and said composition further comprises microcrystalline cellulose; and wherein said tablet leaves an average residue on the tablet punch of 0.6 $\mu g/cm^2$ per tablet or less.

13. The composition according to claim 1, wherein said tablet is a round tablet having a diameter of 20 mm.

14. An oral pharmaceutical tablet composition comprising an effective amount of crystalline Form I amlodipine free base and at least one pharmaceutically acceptable excipient; wherein said tablet leaves an average residue of amlodipien on the tablet punch of 0.7 $\mu g \cdot cm^{-2}$ per tablet or less.

15. The pharmaceutical composition according to claim 14, which further comprises an ACE-inhibitor or a cholesterol-lowering agent.

16. The pharmaceutical composition according to claim 15, wherein said ACE-inhibitor is benazepril and said cholesterol-lowering agent is selected from lovastatin, simvastatin, and atorvastatin.

17. The pharmaceutical composition according to claim 16, wherein said composition comprises said cholesterol-lowering agent selected from lovastatin, simvastatin, and atorvastatin.

18. The pharmaceutical composition according to claim 14, which further comprises benazepril hydrochloride.

* * * * *